United States Patent [19]
Haugen

[11] Patent Number: 5,245,176
[45] Date of Patent: Sep. 14, 1993

[54] METHOD FOR SCANNING PHOTODIODES UTILIZING A SHUTTER MECHANISM HAVING OPENING AND CLOSING TRANSITION TIMES

[75] Inventor: Douglas G. Haugen, Durham, N.C.
[73] Assignee: Akzo N.V., Ls Arnhem, Netherlands
[21] Appl. No.: 896,579
[22] Filed: Jun. 10, 1992
[51] Int. Cl.⁵ .............................................. H01J 40/14
[52] U.S. Cl. ................................ 250/208.3; 250/229; 354/431
[58] Field of Search .................. 250/208.1, 208.3, 229; 356/225, 328; 358/213; 354/226, 410, 429, 430, 431, 432, 433, 434

[56] References Cited
U.S. PATENT DOCUMENTS

| | | | |
|---|---|---|---|
| 4,092,632 | 5/1978 | Agulnek | 340/146.3 |
| 4,264,161 | 4/1981 | Hosoe et al. | 354/31 |
| 4,685,801 | 8/1987 | Minekane | 356/328 |
| 4,718,762 | 1/1988 | Wiget et al. | 356/319 |
| 5,002,392 | 3/1991 | Swope et al. | 356/328 |

Primary Examiner—David C. Nelms
Assistant Examiner—T. Davenport
Attorney, Agent, or Firm—Spencer, Frank & Schneider

[57] ABSTRACT

A method for electronically scanning a photodiode array that is sequentially illuminated by individual light beams by way of a shutter mechanism that has opening and closing transition times during which each light beam is only partially projected onto the array. An integrating light projected on the respective photodiodes of the photodiode array by each light beam over a predetermined period of time beginning after the opening transition time when the shutter mechanism is fully open and ending prior to initiation of the closing transition time while the shutter mechanism is still fully open and producing electrical signals corresponding to the light integrated by the respective photodiodes over the predetermined period of time and storing the electrical signals for subsequent use.

17 Claims, 9 Drawing Sheets

METHOD FOR SCANNING PHOTODIODES UTILIZING A SHUTTER MECHANISM HAVING OPENING AND CLOSING TRANSITION TIMES

BACKGROUND OF THE INVENTION

The invention relates to a method for electronically scanning a light integrating photodiodes, and in particular to a method for electronically scanning one or more photodiode arrays each of which is time shared by a plurality of light beams.

U.S. Pat. No. 5,002,392, the disclosure of which is incorporated herein by reference, discloses a multichannel optical monitoring system in which a plurality of photodiode arrays are illuminated by light beams projected onto the arrays by way of a shutter mechanism. Groups of individual beams are projected onto respective ones of the arrays, and within each group of beams, the beams are sequentially projected onto an array, so that each array is time shared by a group of beams.

Each of the light beams constitutes an optical channel and passes through a reaction well of a cuvette and then through a transmitting diffraction grating for the purpose of performing an optical analysis of a reaction volume in the reaction well. The photodiode arrays each develop electrical signals corresponding to the spectral distribution of the respective beams falling on the arrays, and the arrays are periodically read by electronic scanning circuitry.

The shutter mechanism disclosed in the aforementioned patent comprises a rotating shutter which includes a number of cam elements mounted on a motor driven shaft. The light beams are incident on the cams in a direction parallel to the rotational planes of the cams. Each cam element is aligned in a respective one of the optical channels and has a cut-out segment greater than 180 so that each cam will block the light beam that it is aligned with for a certain portion of the rotation and will pass the beam for a remaining portion of the rotation. The cut-out segments of the cams are angularly arranged relative to one another so that the rotating shutter sequentially passes the beams in a predetermined sequence.

Each cam thus constitutes a shutter element which opens and closes an optical path during each revolution. Actually, each revolution of a cam may be divided into four periods. A first period occurs during a portion of a turn when the cam completely blocks the optical path of the light beam. A second period occurs when an edge of the cam bordering on the cut-out segment passes through the optical path of the beam during which the optical beam is partially transmitted onto the photodiode array. This is the opening transition. A third period occurs at the conclusion of the opening transition when the cut-out segment of the cam is positioned so that the optical path of the beam is uninterrupted by the cam and therefore the entire beam is fully projected onto the photodiode array. The fourth period is the closing transition period when the other edge of the cut-out segment passes through the optical path of the beam so that the optical beam is again only partially transmitted onto the photodiode array. At the conclusion of the closing transition period the optical beam is totally blocked so that the optical channel enters into a dark period (the first period described above) until the next opening transition period.

The electronic scanning circuitry disclosed in U.S. Pat. No. 5,002,392 involves a charge storage mode of operation whereby each photodiode element integrates light projected thereon by virtue of an electron depletion of its p-n junction which is replenished at the time of scanning. The amount of charge required to replenish the electron depletion is a measure of the integrated light. The charge coupled mode of operation for electronically scanning a photodiode array is well known as disclosed in U.S. Pat. No. 5,002,392 and the prior art cited therein.

The charge storage mode of operation for scanning the photodiode arrays is desirable in an environment in which there are hundreds of low level optical signals that must be evaluated at high speeds and is economical in terms of cost and space since only a single charge coupled amplifier is required in lieu of a separate amplifier for each photodiode element.

In the course of developing a machine utilizing the electronic scanning disclosed in U.S. Pat. No. 5,002,392, a number of practical problems evolved. For example, the light on a photodiode array was integrated during the entire time each rotating shutter element was open, including the opening and closing transition times. Theoretically, the opening and closing transition times should be consistent from revolution to revolution, however, in practice it was found that a slight amount of motor jitter introduced jitter into the optical signal from scan to scan. That is, as a result of motor jitter in the motor driving the rotating shutter, the opening and closing transition times would vary from revolution to revolution, resulting in a different amount of light being integrated from scan to scan, with the characteristics of the optical path otherwise being unchanged. Variation in the integration time from scan to scan thus introduced an error into the signal that was being measured, making it difficult to precisely determine what was happening in the reaction volume of the cuvette.

It is was further discovered that in connection with the time sharing of the photodiode arrays with a plurality of optical channels, there were residual effects from brightly lit previous channels observed in succeeding channels, thus further clouding the measured signal.

It was also found that the intensity of light in the outer light channels was not as great as the intensity of light in the central light channels. However, it is desirable that the light channels be balanced in order to stay within the gain limits of the amplifiers of the scanning circuitry.

Another practical problem that developed concerned the amount of time that was available for the host computer to collect data and calculate gain values for the next scan. Specifically, the data collected during each scan is stored in a buffer memory prior to being forwarded to the host computer. In that no scan data can be stored in the buffer memory at the same time data is being acquired from the buffer by the host computer, and concomitantly a finite period of time is required to empty the buffer register, it is important that sufficient data acquisition time, i.e. the time required to empty the buffer register into the memory of the host computer, be available in order that all scan data stored in buffer memory be utilized by the host computer. It is thus desirable to optimize the scanning sequence in order to provide as much data acquisition time as reasonably possible.

SUMMARY OF THE INVENTION

It is an object of the present invention to provide a method of scanning a photodiode array which avoids the problems discussed above, and in particular avoids the effects of motor jitter on the scan signal.

It is a further object of the invention to eliminate the residual effects from brightly lit previous channels in a photodiode that is time shared by a plurality of beams.

It is another object of the invention to optimize the electronic scanning of a plurality of photodiode arrays in a manner that increases the available data acquisition time for transferring scan data from a buffer memory to a host computer.

The above and other objects are accomplished in accordance with the invention by a method for electronically scanning a photodiode illuminated by a light beam by way of a shutter mechanism that has opening and a closing transition times during which the light beam is partially projected onto the array, with the shutter mechanism being fully open for a period of time between the opening and closing transition times for fully illuminating the photodiode with the light beam, the method comprising steps of:

integrating light projected on the photodiode by the light beam over a predetermined time interval beginning after the opening transition time when the shutter mechanism is fully open and ending prior to initiation of the closing transition time while the shutter mechanism is still fully open; and producing electrical signals corresponding to the light integrated by the photodiode over the predetermined time interval.

According to another aspect of the invention there is provided a method for electronically scanning a time-shared photodiode array that is sequentially illuminated by individual light beams by way of a shutter mechanism that has opening and closing transition times during which the individual light beams are partially projected onto the array, with the shutter mechanism having a fully open period between the opening and closing transition times when the array is fully illuminated by the light beam, the method including steps of: starting a light integration period for each light beam projected onto the photodiode array after the opening transition time when the shutter mechanism is fully open; ending the light integration period after a predetermined time and before initiation of the closing transition time while the shutter mechanism is still fully open; and producing signals corresponding to the light integrated by each of the photodiodes of the array at the end of the light integration period.

Thus, by integrating light only over a predetermined period of time during which the shutter is fully open, the effects of motor jitter which may extend or shorten the opening and closing transition periods of each shutter element are completely avoided.

Further, in accordance with another aspect of the invention, the photodiodes are scanned during a dark period between consecutive light beams projected onto the array to reset the photodiodes in the dark. This minimizes the carryover effects of a brightly lit previous channel time sharing the same array.

In accordance with another aspect of the invention, a plurality of photodiode arrays are arranged for illumination by a different group of individual beams and the individual beams of each group are sequentially projected onto a respective one of the arrays and each array is scanned in the same manner as above with the method further including selectively setting a predetermined time interval for integrating the light beams on each of the photodiode arrays. This aspect of the invention permits the channels to be balanced relative to one another even though the light intensity among the channels is not uniform. For example, in the context of a multi-channel analyzer of the type described in U.S. Pat. No. 5,002,392, if the light is brighter in the inner or central channels than at the outer channels, the scanning mechanism according to the invention allows the integration time for the outer channels to be extended and the integration time for the central channels to be reduced to balance the electrical signals produced when the arrays are scanned. Balancing the signals in this manner makes them more compatible with the range of amplifier gain in the electronic circuitry following the charged coupled amplifier.

Other objects, features and advantages of the invention will become apparent from the following detailed description taken in conjunction with the drawings.

DETAILED DESCRIPTION OF THE PREFERRED EMBODIMENT

Figure 1:
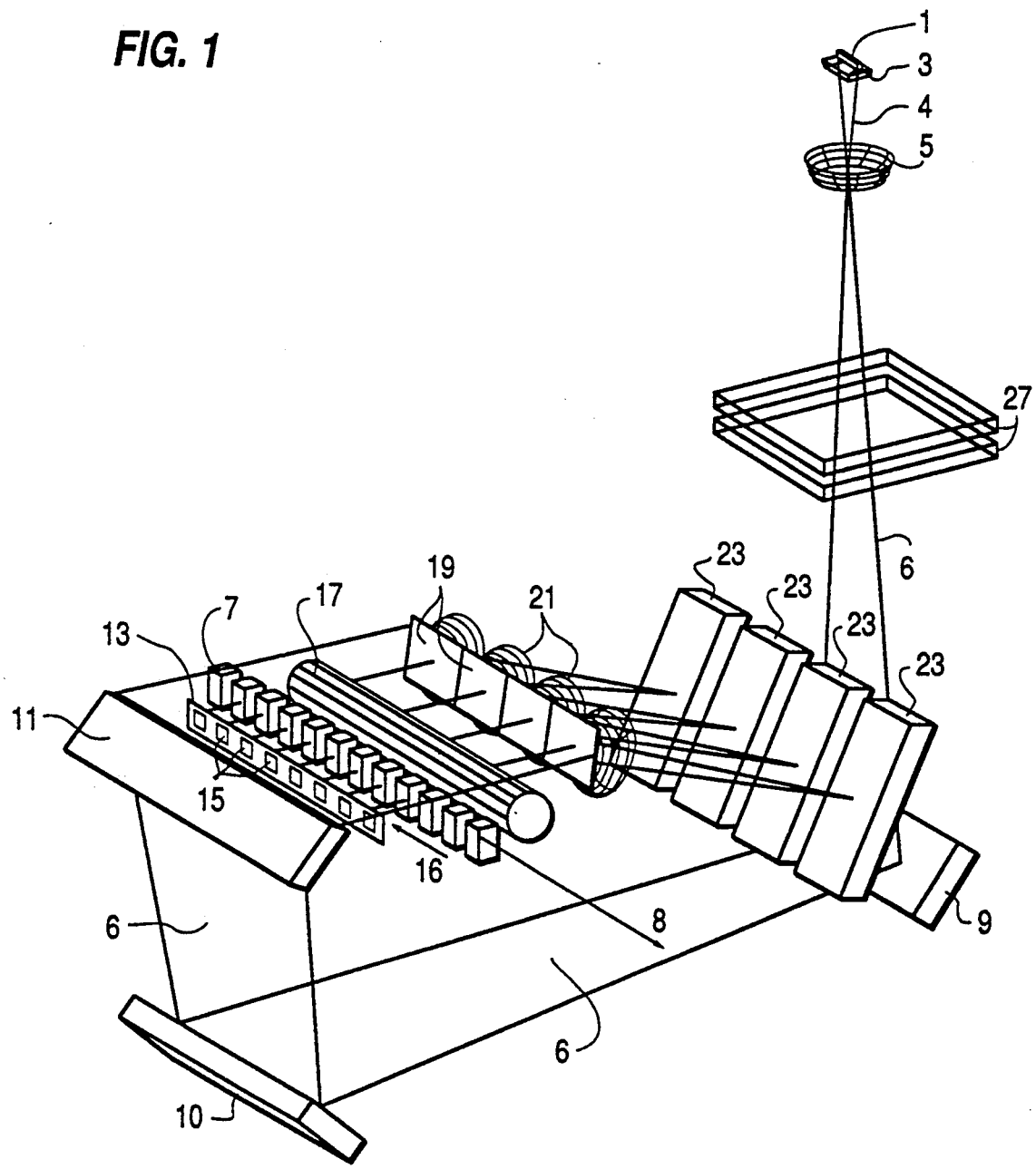
FIG. 1 is a schematic showing a known embodiment of an optical monitoring system for which the scanning method according to the invention is useful.

FIG. 1 is a schematic of a multi-channel optical analyzer with which the scanning method of the present invention may be utilized. The multi-channel optical analyzer illustrated in FIG. 1 is described in greater detail in U.S. Pat. No. 5,002,392, which is incorporated herein by reference, and will only briefly be described herein to the extent necessary for understanding the present invention.

As shown in FIG. 1, a broadband spectral light source 1 projects light towards a slit forming device 3 which passes a beam 4 having the pattern of a slit. A short focal length collimator 5 follows the slit and is used to project the beam 4 in a pattern of a slit to infinity, thereby forming a slowly diverging beam 6. Beam 6 is shown to be folded a number of times by mirrors 9, 10 and 11 prior to being intercepted by a mask 13 having a plurality of openings 15 for dividing beam 6 into a plurality of individual beams 16 corresponding to the number of reaction wells 7 containing reaction volumes to be optically monitor. Reaction wells 7 are moved incrementally in the direction of arrow 8 from station to station, each station corresponding to the optical path of a respective one of the individual beams 16. The respective optical beams are also referred to herein as light channels. Although only 8 light channels are illustrated in FIG. 1, the number of light channels built into a machine is a design choice. For example in one implementation of the machine developed by the assignee of the present application, there were 15 light channels, meaning that there were 15 light beams formed by mask 13 and each reaction well of a cuvette was moved incrementally through each light channel, residing at each station or channel long enough for the reaction volume to be optically monitored to detect any change in the spectrum of the light beam transmitted therethrough.

After passing through reaction wells 7, beams 16 are intercepted by a rotating shutter 17 which sequentially passes the beams transmitted by the reaction volumes in reaction wells 7. The beams passing through shutter 17 are diffracted by transmitting diffraction gratings 19 in a know manner. FIG. 1 shows four diffraction gratings 19 followed by four corresponding focussing lenses 21 for focussing the diffracted beams onto four corresponding photodiode arrays 23. Again, the number of diffraction gratings, focussing lenses and photodiode arrays is a design choice depending on how the light channels are to be time shared. Photodiode arrays 23 are arranged so that the spectrum of each diffracted beam falls across the linearly arranged photodiode elements of a respective one of the arrays. The optics of the system are such that a central element of each array 23 is the optical conjugate of slit 3. Photodiode arrays 23 each develop electrical signals corresponding to the spectral distribution falling on the array. Arrays 23 are connected to scanning and recording electronics which sequentially scan the photodiodes for converting the electrical signals to digital signals and storing the digital signals in a computer memory for further processing and evaluation.

Figure 2:
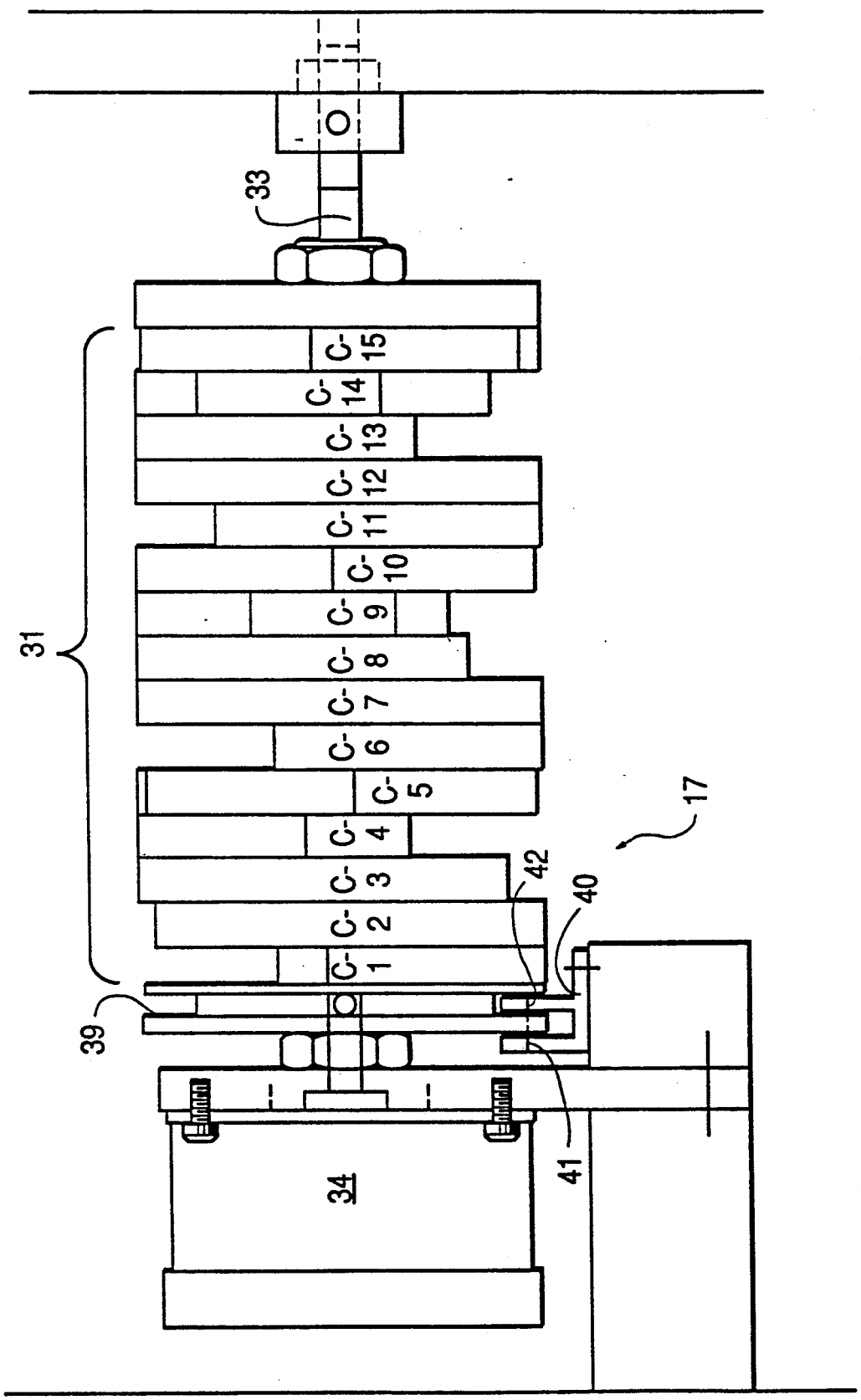
FIG. 2 is a front elevational view of a known rotating shutter used in the system of FIG. 1.

As shown in FIG. 2, rotating shutter mechanism 17 comprises a number of cam (shutter) elements 31 mounted on a shaft 33, driven by a motor 34. FIG. 2 shows 15 cam elements 31, numbered C-1 through C-15, which are arranged in the optical monitoring system so that they are each aligned with a respective one of beams 16 passing through windows 15 of mask 13 shown in FIG. 1. Each cam element 31 has a sector removed so that upon rotation of shutter mechanism 17 each one of the beams 16 is either blocked or passed depending on the rotational position of the respective cam element. The same size sector, for example 240° is cut out of each cam. Cams 31 are fixed to shaft 33 so that the cut-out sectors are angularly arranged relative to one another to produce a desired timing sequence in which beams 16 are passed to photodiode arrays 23.

Figure 3:
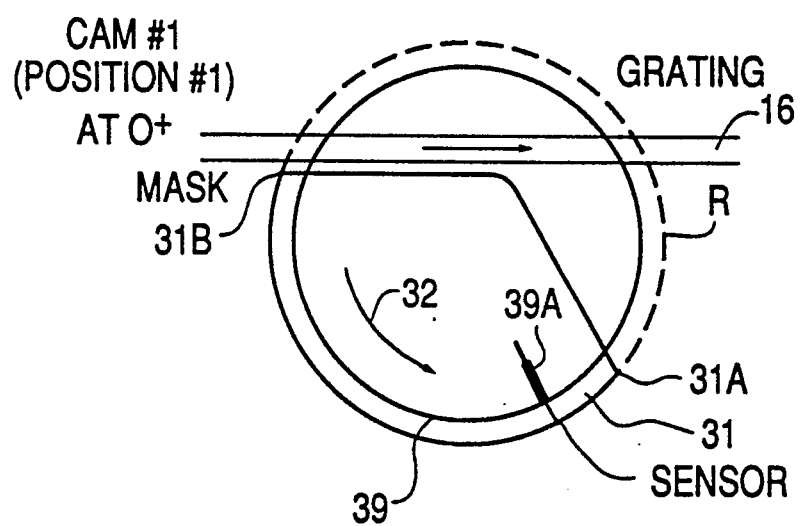
FIG. 3 is a schematic view to explain the operation of the rotating shutter illustrated in FIG. 2.
Figure 4A:
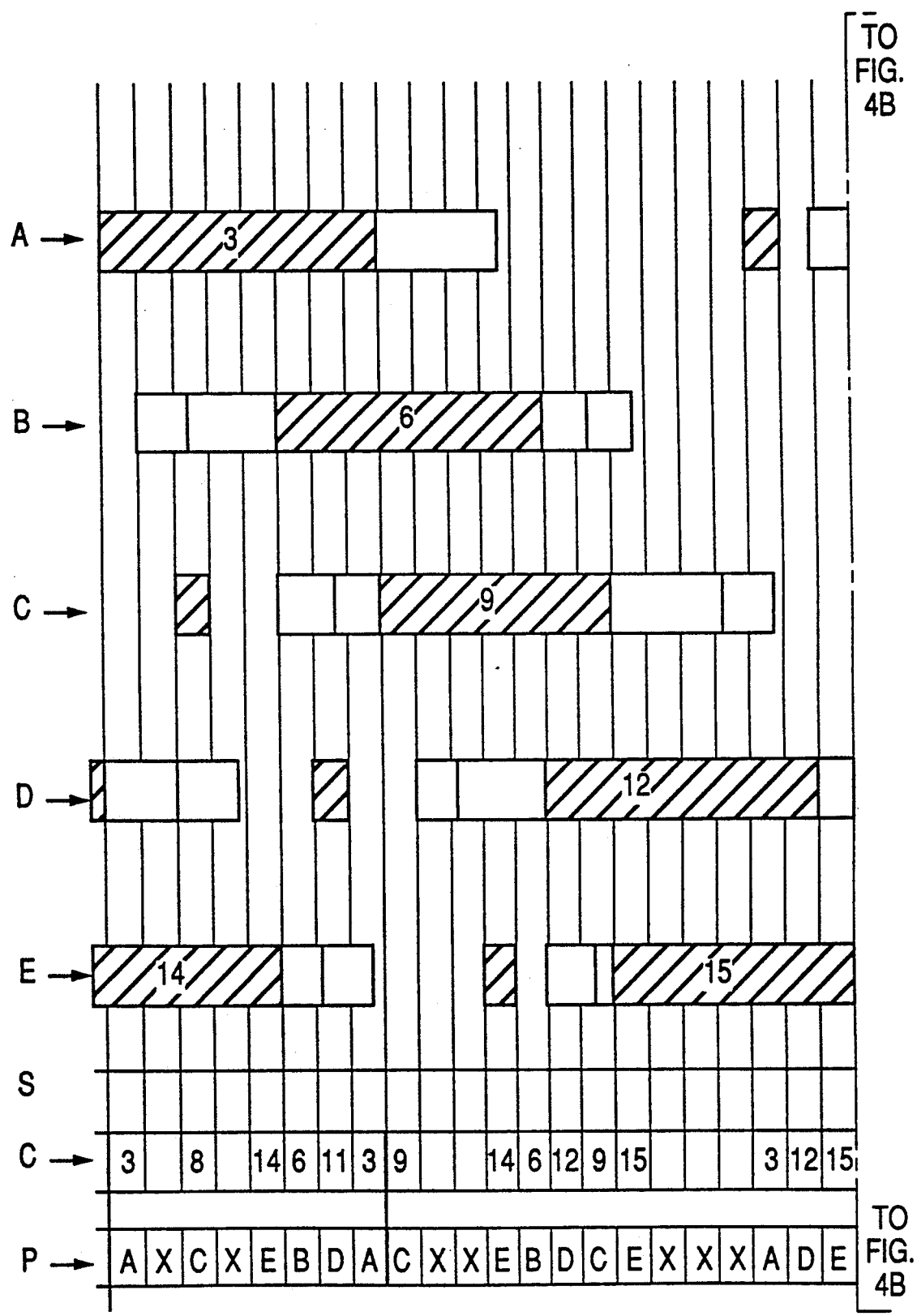
FIGS. 4a–4e are timing diagrams used to explain the operation of the rotating shutter and the principle of operation of the scanning method according to the invention.
Figure 4B:
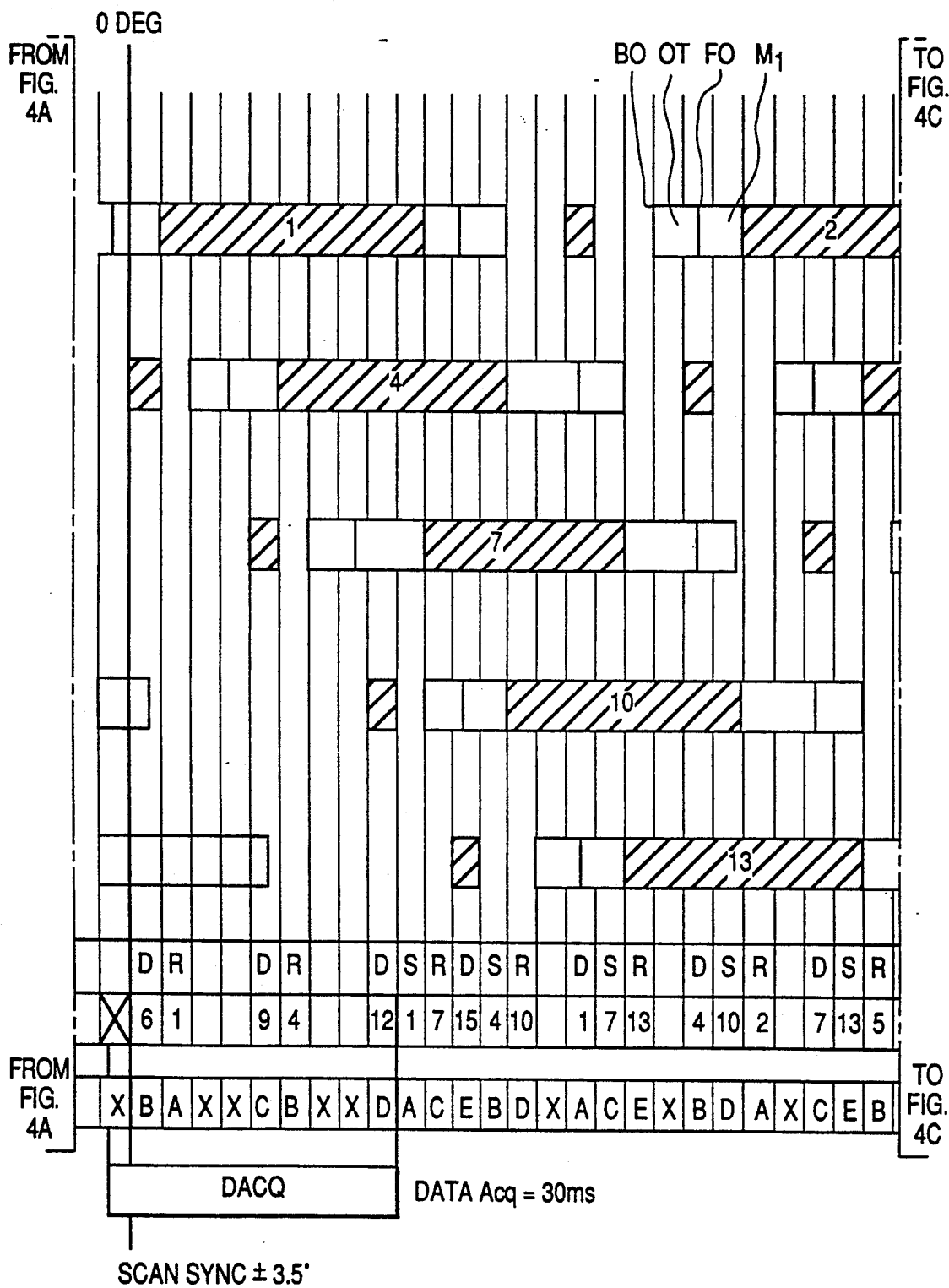
Figure 4C:
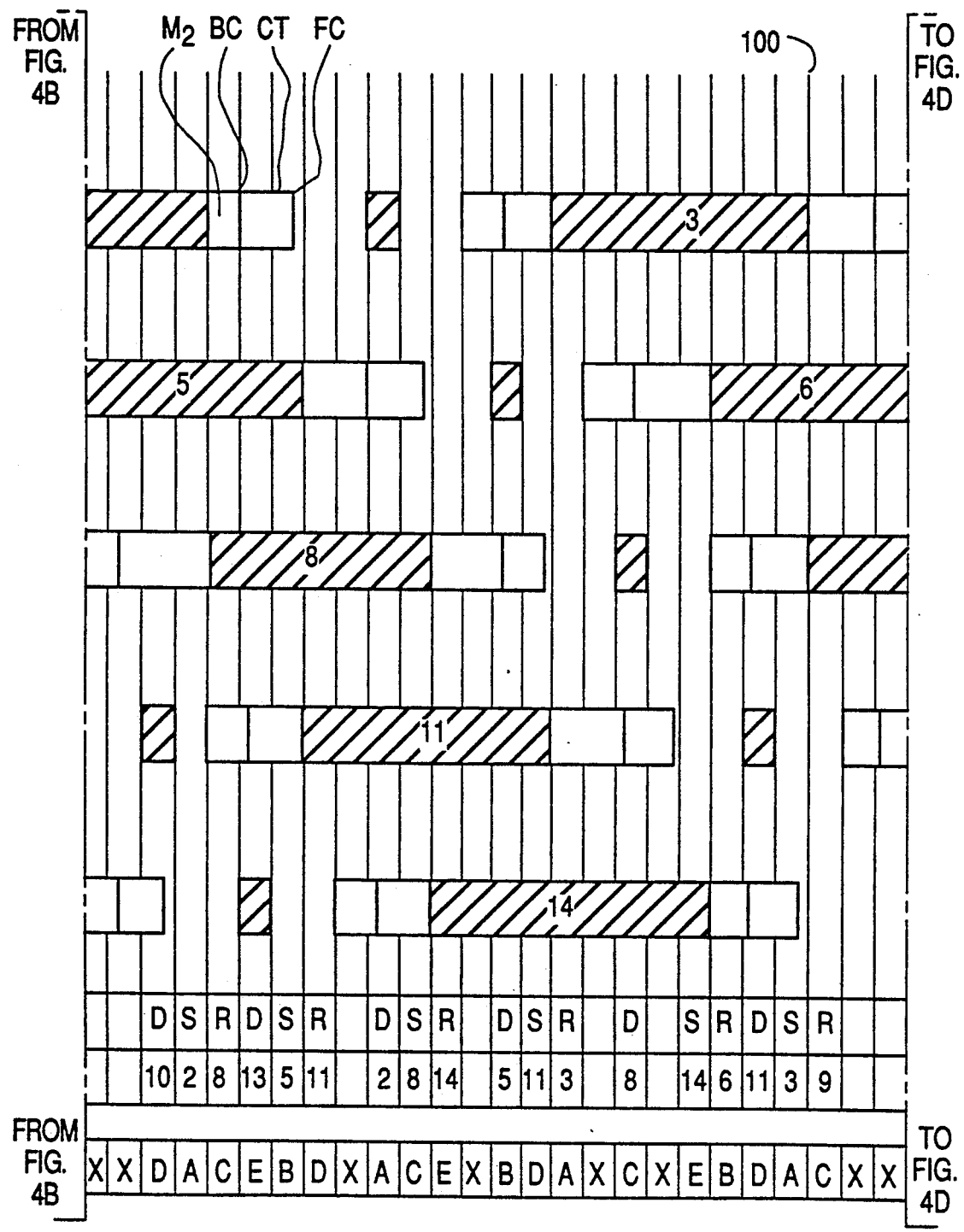
Figure 4D:
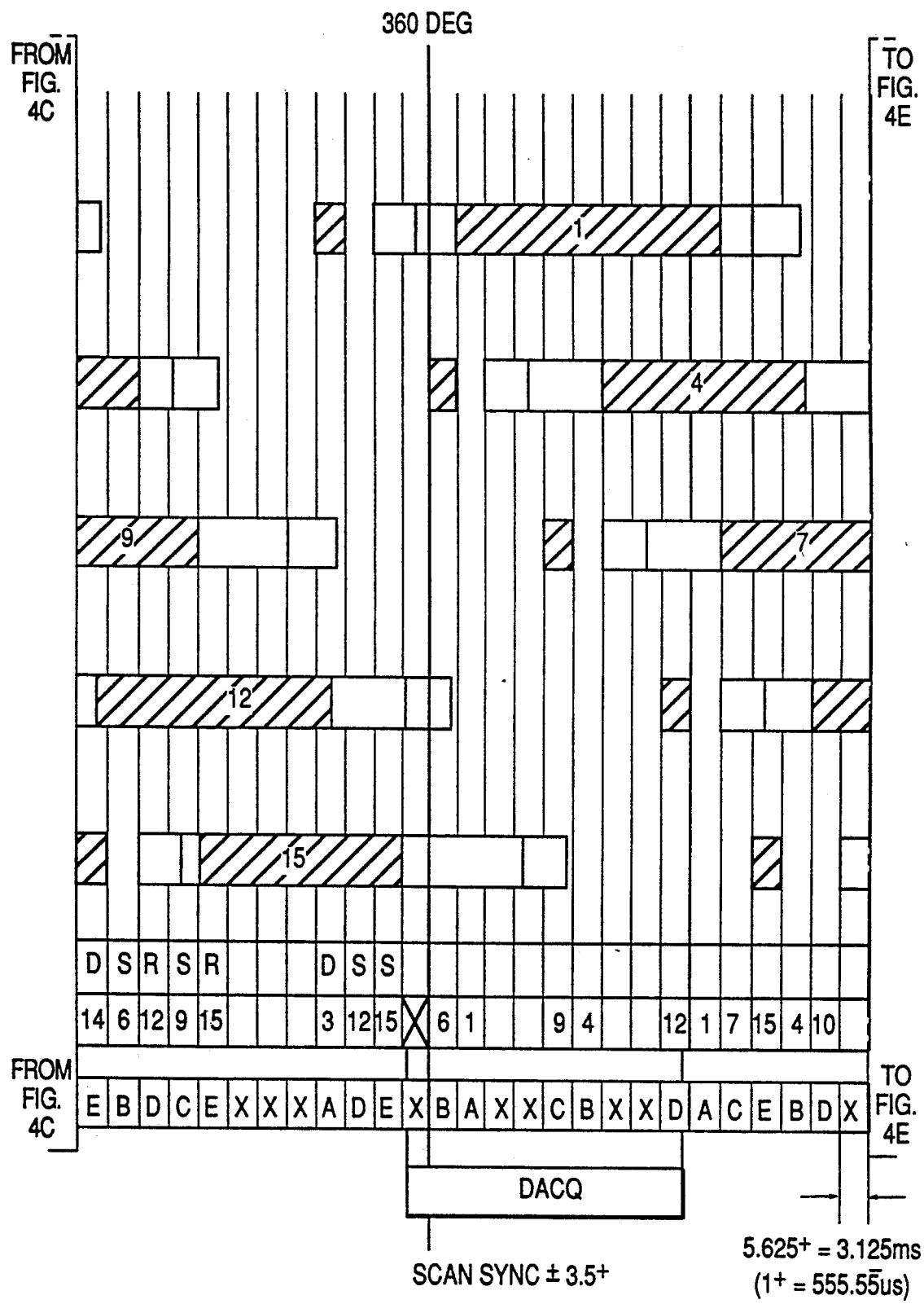
Figure 4E:
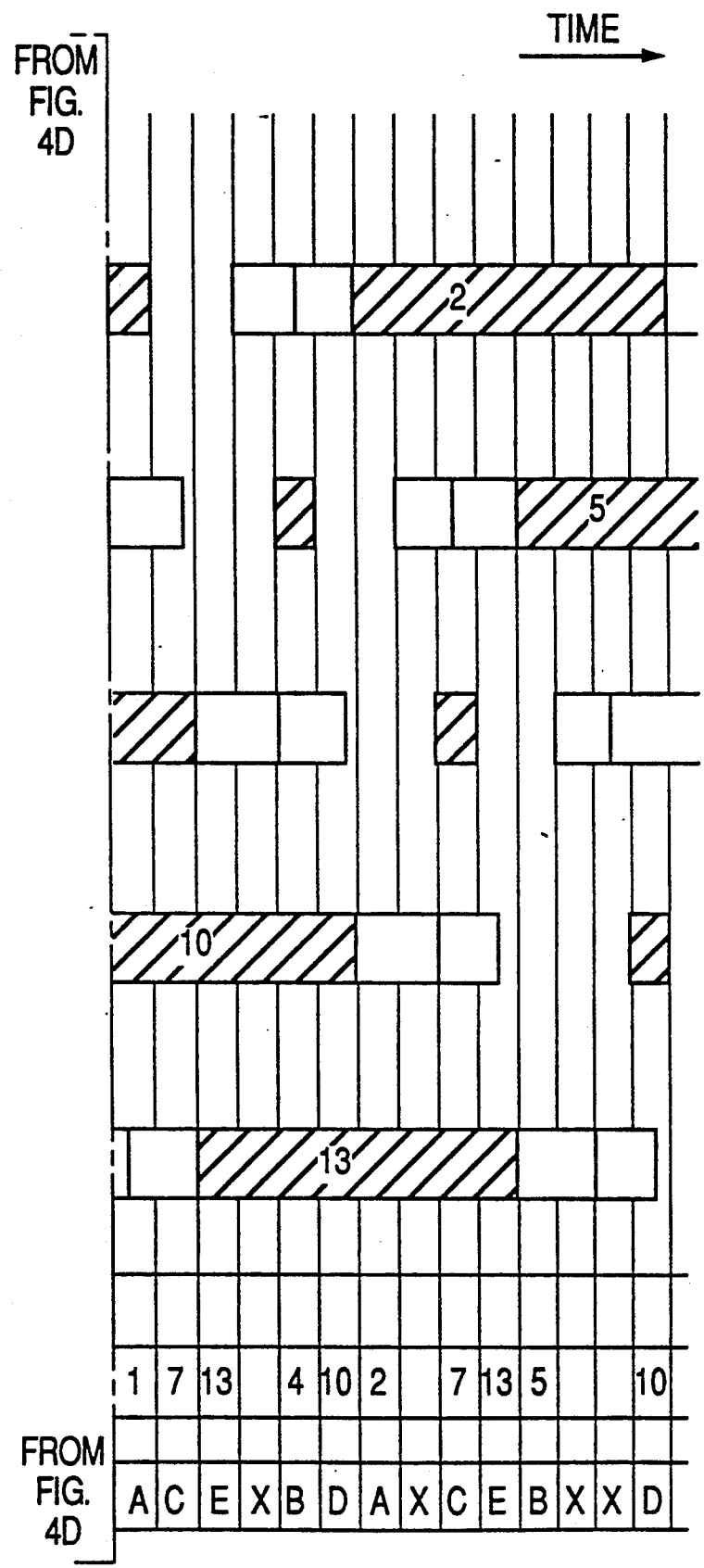

FIG. 3 shows a representative cam element 31, specifically cam C-1, in the first position on the far left in FIG. 2. As shown in FIG. 3, cam element C-1 is in the fully opened position for transmitting light beam 16. It may be appreciated that as the cam element rotates in the direction of arrow 32, edge 31A of the cam element will intercept beam 16 in a gradual manner where it exits the circle of revolution R of the cam element to progressively block beam 16 until the beam is fully blocked by the cam element. This is referred to herein as the closing transition period of the cam element. As the cam element continues to rotate, an edge 31B of the cam element will pass through beam 16 where it is incident of the circle of revolution R of the cam element to progressively open the transmission path of the beam until the beam is fully transmitted through the cam element as shown in FIG. 3. This is referred to herein as the opening transition period of the cam element.

Referring jointly to FIGS. 2 and 3, an opto-electronic circuit 40, including an optical transmitter 41, directs a light beam toward an optical receiver 42. This beam is interrupted by a sync disk 39 except for the time when a slot 39A in such disc 39 is in the optical path between optical transmitter 41 and optical receiver 42. An electrical synchronization signal is therefore developed by optical receiver 42 each time slot 39A passes through the beam. The sync signal produced by optical receiver 42 is fed to the scanning circuitry as will be described hereafter.

FIGS. 4a–4e illustrates an exemplary shutter and scanning timing diagram from which the principles of operation of the method according to the invention will become apparent. The timing diagram illustrated in FIGS. 4a–4e are based upon an example in which there 15 light beams (channels) L-1 to L-15 and five photodiode arrays 23, namely arrays A-E. In this example each photodiode array A-E is time-shared by three beams 16 which are sequentially projected onto a respective one of the photodiode arrays by way of an optical system such as that illustrated in FIG. 1 utilizing a shutter mechanism such as that illustrated in FIG. 2. Thus, photodiode array A sequentially receives beams L-1 to L-3, photodiode array B sequentially receives beams L-4 to L-6, photodiode array C sequentially receives beams L-7 to L-9, photodiode array D sequentially receives beams L-10 to L-12, and photodiode array E sequentially receives beams L-13 to L-15 by way of rotating shutter mechanism 17, diffraction gratings 19 and focussing lenses 21. The 0° and 360° lines are time reference positions resulting from rotating synch disc 39. The vertical time division lines 100 are separated by 3.125 ms which corresponds to the timing produced by a electronic clock driving the scanning circuitry described below. The shutter and scan timing illustrated between 0° and 360° in FIGS. 4a–4e from each full rotation of the shutter mechanism illustrated in FIG. 2. Thus, during each rotation of shutter mechanism 17, each photodiode array A-E is time-shared by 3 light beams or light channels as previously discussed.

Reference is now made to light beam L-2 illuminating photodiode array A for purposes of explaining the timing diagram. The transmission of light beam L-2 is controlled by the rotation of cam element C-2. Light beam L-2 has an opening transition period OT, beginning at time BO, during which light beam L-2 is only partially passed by cam element C-2 onto photodiode array A until a time FO when cam element C-2 is in a fully opened (non-blocking) position for transmitting the entire light beam onto photodiode array A. Cam element C-2 remains in a fully open, non-blocking position until a time SC when its edge 31A (FIG. 3) begins to move into the path of the light beam to start the closing transition time CT which is terminated at time FC when light beam L-2 is fully blocked. The cross-hatched portion between the FO and BC time marks represents the period during which the photodiode array is actually integrating light. As can be seen, light integration begins after a time margin M1 and ends prior to a time margin M2. Time margins M1 and M2 are built-in time periods just after the cam reaches its fully open position and just before the cam element starts its closing transition to ensure that light integration occurs during a period in which the light path through cam element C-2 is uninterrupted. The foregoing discussion of light beam 2 applies to each of the other light beams, the important point being that light is only integrated during a period in which the respective cam element presents a fully open light path. Thus, any effects due to jitter of the motor driving the rotating shutter mechanism are completely eliminated in that no light is integrated during the opening and closing transition times, but rather only during a time when each cam element is in a fully open position as discussed above.

Each light integration period is begun by resetting the photodiode array and is terminated by scanning the photodiode array and producing signals representing the amount of light integrated by each of the photodiode elements in the array.

The scanner electronics are based on the charge storage mode of operation of the photodiode array. In the charge storage mode of operation, a photodiode integrates the photon to electrical conversion over a predetermined time period in that as light strikes each photodiode of the array, electrons are driven out of the p-n junction by photons. The charge stored in the parasitic capacitance of the photodiode becomes depleted of charge carries with increasing light. The amount of charge lost is determined by measuring how much charge it takes to fully (or nearly fully) recharge the photodiode element which is accomplished by a charge coupled amplifier connected to the diode. The output of the charge coupled amplifier replicates the integrated electrical signal.

The operation by which the photodiode array is reset is actually performed by scanning the photodiode array whereby charge depleted from each of the photodiodes is replenished so that light integration begins at an initial charge level. At the conclusion of the light integration period, the photodiode array is again scanned according to the charge storage mode of operation. The difference between the scan performed at the beginning of light integration to reset the photodiode array and the scan performed at the end of light integration period is that the signals representing a measure of the lost charge produced at the end of the light integration period are stored. On the other hand, the scan signals produced at the beginning of light integration during the reset operation are not stored.

In accordance with a further aspect of the invention, each photodiode array is scanned during a dark period between the respective light channels illuminating the array. The purpose of the scan during the dark period is to eliminate any shadow or carry-over effect on the array from the previous channel (light beam). Thus, for example, during the dark period between light beams L-2 and L-3, photodiode array A is scanned to replenish any residual depleted charge remaining from light beam L-2 to ensure that photodiode array A is reset at the beginning of the light integration period for light beam L-3 to a repeatable value.

At the lower portion of FIGS. 4a-4e there are three rows across the timing diagram. The center row C indicates the number of the channel, L-1 to L-15, that is being currently scanned, with the prefix "L" being eliminated from the numbers in row C due to space limitations. The bottom row P indicates the photodiode array, A to E, which is being illuminated by the light channel currently scanned. The top row S indicates whether the scan that is currently being performed is during a dark period (D), or for the purpose of resetting (R) the photodiode array, or is an actual scan (S) for valid data during which data representing light integration is stored.

Thus, during the first 3.125 ms time period following the 0° time line, the timing diagram of FIGS. 4a-4e indicate that photodiode array B is being scanned during its dark period between light channel L-6 and L-4. During the second 3.125 ms time period following the 0° time line, photodiode array A is being reset to begin light integration for channel L-1. During the next two 3.125 ms time periods, light from channel L-1 continues to be integrated on photodiode array A, however, none of the photodiode arrays are being scanned for any purpose. This is indicated by the X in the third and fourth boxes following the 0° time line in row P. In the fifth 3.125 ms time period, photodiode array C is being scanned during the dark period following channel L-9. The photodiode arrays continue to be scanned in the sequence indicated by row P.

Valid data is only collected during those time intervals indicated in row S with a (S). As can be seen, the first time a scan produces valid data is at the end of the light integration interval for channel L-1 in the tenth 3.125 ms time period following the 0° time line. A (S) is marked in fifteen of the boxes in row S signifying that the scan of the photodiode arrays conducted during those time periods is for the purpose of collecting valid data representing light integrated on the photodiode arrays.

According to another aspect of the invention, the length of the light integration interval on each of the photodiode arrays is adjusted so that the channels remain relatively balanced in order that the output signals remain compatible with the range of the gain of the amplifiers in the circuitry measuring the signals. That is, it has been found in practice that the intensity of the light in diverging beam 6 in FIG. 1 decreases from a central region to an outer region so that the light intensity on the central channels is more intense than those on the outermost channels. Accordingly, in order to balance the output of the channels, the method according to the invention increases the length of the light integration interval from the central channels L-7, L-8 and L-9 which are integrated on photodiode array C in a gradual manner toward the outermost light channels which are integrated on photodiode array A. Thus, for example, the length of the light integration interval on photodiode array C for channels L-7, L-8 and L-9 may be 18.75 ms, the light integration interval for light channels L-4, L-5 and L-6 on photodiode array B and light channels L-10, L-11 and L-12 on photodiode array D is 21.875 ms and the light integration interval for channels L-1, L-2 and L-3 on photodiode array A and light channels L-13 and L-14 on photodiode array E is 25 ms in the scenario illustrated by the timing diagram of FIG. 3. Light integration on channel L-15 is arbitrarily cut short in order that light integration does not occur during a synch signal.

As can be seen, since no valid data is collected during the ten 3.125 ms intervals following the valid data scan of channel L-15 on photodiode array E, a period of 31.25 milliseconds is made available for data acquisition during which valid data collected during a full rotation of the shutter and stored in a buffer memory may be transferred to a host computer for processing and analyses.

Figure 5:
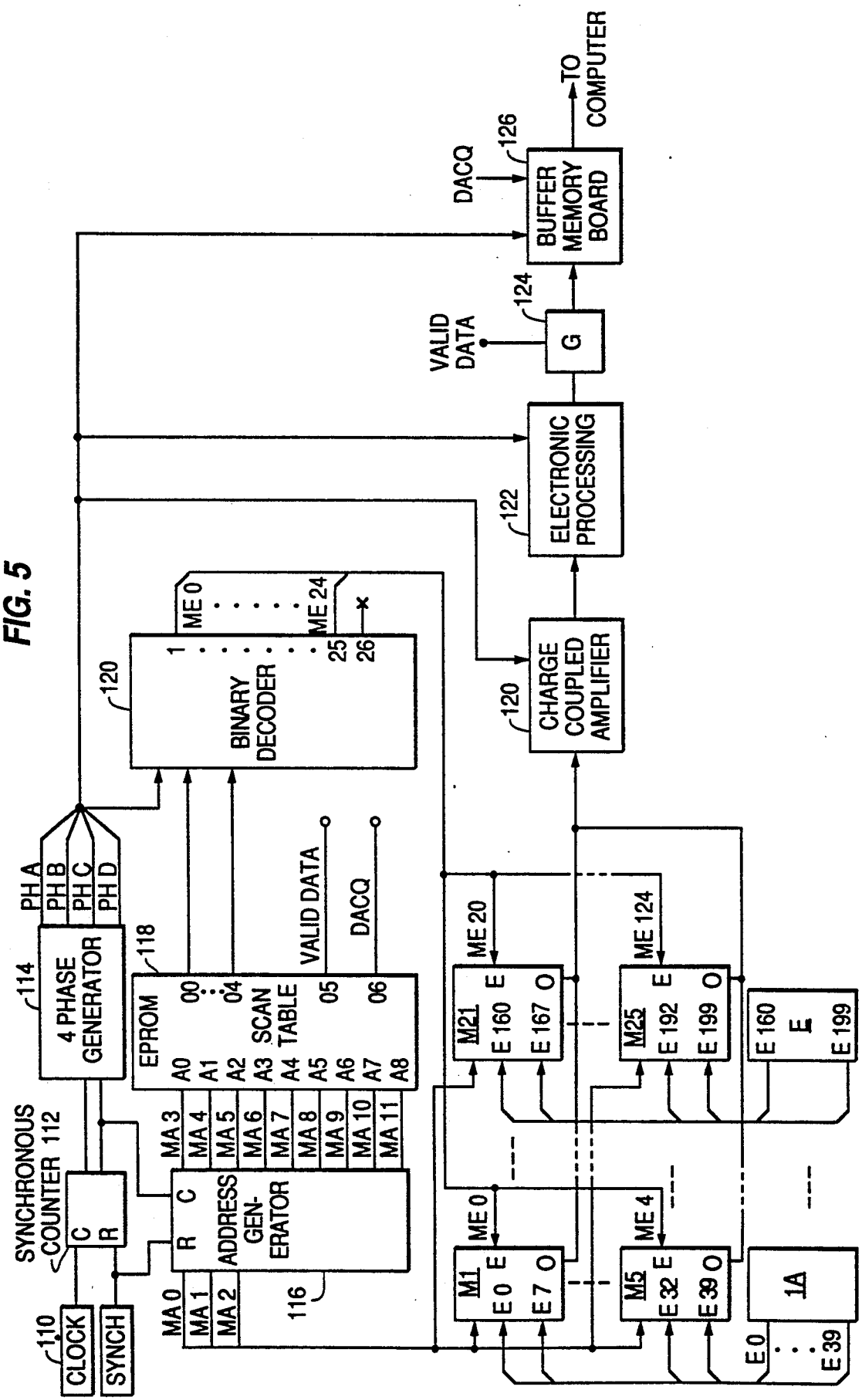
FIG. 5 is a block circuit diagram of an electronic circuit for implementing the scanning method according to the invention.

FIG. 5 shows a block circuit diagram of an electronic circuit which can be utilized to accomplish the scanning of the photodiode arrays as depicted in the timing diagram of FIGS. 4a-4e.

The block circuit diagram of FIG. 5 is similar to the block circuit diagram of FIG. 6 in U.S. Pat. No. 5,002,392 with the principal difference being the use of an EPROM in place of a 12-bit counter for addressing the multiplexers in the appropriate sequence for scanning the photodiode arrays.

As shown in FIG. 5, a clock, which may be in the form of a free running oscillator having a basic frequency of 51.2 KHz, supplies a clock pulse signal to the clock input of a synchronous counter 112, the output of which is fed to a four phase generator 114 as well as an address generator 116. Synchronous counter 112 and address generator 116 are each reset by the synch pulse produced by synch disk 39 on each revolution of rotating shutter mechanism 17.

Four phase generator 114 comprises a decoder which receives the synchronous output of counter 112 and produces four sequential pulses, referred to herein as phases A-D, on separate lines which are used as the basic timing signals for driving the scanner electronics in a manner analogous to that described in U.S. Pat. No. 5,002,392. The scanning of a single photodiode in one of the photodiode arrays requires one complete cycle through all four phases A through D.

Address generator 116 includes a twelve-bit counter, the lower three bits MA0 to MA2 of which are feed to each of twenty-five multiplexers M1 to M25 for selecting 1 of 8 photodiodes in each group of eight photodiodes which are connected to respective ones of the twenty-five multiplexers. Each photodiode array A to E has forty photodiodes for a total of 200 photodiodes which are scanned in twenty-five groups of eight photodiodes per group. The upper eight bits of address generator 116, i.e., bits MA3 to MA11, are input as addresses to EPROM 118 for enabling the appropriate multiplexer.

Binary weighted values stored in the memory cells of EPROM 118 are selectively output to a binary decoder 120 which has twenty-five outputs ME0 to ME24 connected to respective ones of multiplexers M1 to M25 for enabling the multiplexers in a sequence necessary for achieving the scanning depicted in FIGS. 4a–4e. That is, the memory cells of EPROM 118, which are addressed numerically by address generator 116, have binary weighted values, which when decoded, enable the twenty-five multiplexers M1 to M25 in the appropriate order so that photodiode arrays A-E will be scanned in the order and time sequence shown in row P of FIGS. 4a–4e. By virtue of the sequence in which the photodiode arrays are illuminated by the various light channels L-1 to L-15 as shown in row C of FIGS. 4a–4e, each scan of a photodiode array will either be during a dark period, or for resetting the photodiode array at the beginning of a light integration period, or scanning the photodiode array at the end of a light integration period at which time valid integration data is collected. These three different types of scans are depicted in row C in FIGS. 4a–4e as previously discussed.

Valid data is collected during a (S) scan at the end of a light integration period of a given photodiode array by appropriately weighing the binary values stored in the memory cells of EPROM 118 so that in addition to enabling the appropriate multiplexers for scanning the arrays, the 05 output of EPROM 118 is set "high" for producing a valid data signal.

The outputs of multiplexers M1 to M25 are connected to the input of charge coupled amplifier 120. The photodiode elements are thus serially connected to the input of charge coupled amplifier 120 in the sequence determined by the scan table stored in EPROM 118 in combination with the MA0 to MA2 outputs of address generator 116 which cause an enabled multiplexer to cycle through the eight photodiodes to which it is connected. Each time a photodiode is connected to charge coupled amplifier 120, a scan signal is produced at the output of charge coupled amplifier 120 that represents the amount of charge depleted from the p-n junction of the scanned photodiode. When a photodiode is scanned at the end of a light integration period, the scan signal corresponds to the amount of light integrated over the integration period. The output of charge coupled amplifier 120 is input to electronic processing circuitry 122 for amplification, filtering, A/D conversion, etc., in a manner analogous to that described in U.S. Pat. No. 5,002,392. As discussed above, scans performed at the conclusion of a light integration period are accompanied by a valid data signal which enables a gate 124 connected between the electronic processing circuitry and a buffer memory board 126 so that the scan data can be temporarily stored locally before being transferred to a host computer (not shown) during a data acquisition period.

During the data acquisition period which, as shown in FIGS. 4a–4e, extends from the end of the light integration period for light channel L-15 and the dark scanning period for channel L-12, the appropriate memory cells in EPROM 118 are weighted with a binary value which will ensure that output 06 of EPROM 118 is set "high" to produce a data acquisition signal for causing buffer memory board 122 to output its data to the host computer.

The operation of the scanning electronics illustrated in FIG. 5 will now be described by way of example. Assume that a synch pulse has just been produced for resetting synchronous counter 112 and address generator 116 so that the scanning sequence illustrated in FIGS. 4a–4e is at 0° time line. As shown in FIGS. 4a–4e, at this point in time, light channel L-1 is fully illuminating photodiode array A, scanning of photodiode array B during a dark period is initiated between light channels L-6 and L-4, photodiode array C is experiencing a dark period between light channels L-9 and L-7, photodiode array D is in a closing transition period with regard to light channel L-12, and photodiode array E is fully illuminated by light channel L-15 but has already been scanned for valid data.

In order for the forty photodiode elements of photodiode array B to be scanned, it is necessary to sequentially enable multiplexers M6–M10. Each multiplexer M6–M10 sequentially connects eight diodes of photodiode array B to charge coupled amplifier 120. By sequentially enabling multiplexers M6–M10 all photodiode elements of photodiode array B will be scanned.

Scanning photodiode array B during a dark interval as well as during the data acquisition interval will require a binary weight in the first cell addressed by address generator 116 that will set the data acquisition output of EPROM 118 "high", set the valid data output "low", and enable the ME5 output of binary decoder 120. Multiplexer M6 stays enabled until inputs MA0--MA2 cycle through eight photodiode elements of photodiode array B. The outputs of the first eight photodiode elements E160 to E167 of photodiode array B are thus sequentially coupled to charge coupled amplifier 120 which in a known manner replenishes charge depleted from the photodiode element and produces an output which is a measure of the depleted charge. The output of charge coupled amplifier 120 is then electronically processed in a manner analogous to that described in U.S. Pat. No. 5,002,392, however, the data does not go anywhere since gate 124 is not enabled by a valid data signal. The remaining photodiode elements of photodiode array B are scanned in a similar manner by sequentially enabling multiplexers M7-M10. This is done by increasing the binary weight by one in the next four memory cells of EPROM 118 which are addressed by address generator 116.

Referring to row P of FIGS. 4a-4e, the second photodiode array to be scanned after the 0° time line is photodiode array A which is scanned to reset the photodiode elements thereof to initiate a light integration interval for light channel number L-1. Thus, the next five memory cells in EPROM 118 which are sequentially addressed by address generator 116 have binary weights which will sequentially enable multiplexers M1-M5 and continue to set the data acquisition output signal of EPROM 118 to a high level and the valid data output to a low level. The photodiode arrays continue to be scanned in the sequence indicated by row P of FIGS. 4a-4e by virtue of the scan table programmed in EPROM 118. The (S) scan performed at the end of each light integration interval for the respective light channels requires that the valid data output of EPROM 118 be set high in order to enable gate 124 so that the signals at the output of charge coupled amplifier 120, which represent a measure of the light integrated by the respective photodiode elements of an array, are stored in buffer memory board 126.

As discussed previously, four phase generator 114 sets the basic timing for the scanning electronics illustrated in FIG. 5. During phase A the integrating capacitor (not shown) of the charge couple amplifier 120 is reset so that during phase B charge couple amplifier 120 is ready to accept signals from the photodiode elements currently being scanned. During phase C the appropriate multiplexer is enabled by the output of binary decoder 120 so that the eight photodiode elements to which that multiplexer is connected are sequentially connected to the charge coupled amplifier under control of the MA0-MA2 inputs to the multiplexer. During phase D, the signals are passed through electronic processing circuitry 122 during which the signals are amplified, filtered and converted to digital signals in a manner analogous to that disclose in U.S. Pat. No. 5,002,392. The data is then passed to and stored in buffer memory board 122 only if there is a valid data signal V to open gate 120, which occurs only when the photodiode elements are being scanned at the end of light integration intervals as indicated in FIGS. 4a-4e. As discussed previously, after valid data has been stored in buffer memory board 126 for all fifteen light channels, EPROM 118 is programmed to produce a data acquisition signal DACQ to allow the data stored in the buffer memory board to be transferred to a host computer. As shown in FIGS. 4a-4e, the DACQ signal is present for the interval beginning just after the (S) scan of photodiode array E at the conclusion of the light integration period for channel L-15 and just prior to the (S) scan of photodiode array A at the conclusion of the light integration period of channel L-1. The data acquisition interval thus covers about ten of the 3.125 time intervals shown in FIGS. 4a-4e which provide adequate time for transferring the data from the buffer memory board to the host computer.

It will be understood that the above description of the present invention is susceptible to various modifications, changes and adaptations, and the same are intended to be comprehended within the meaning and range of equivalents of the appended claims.

What is claimed is:

1. A method for electronically scanning a photodiode illuminated by a light beam by way of a shutter mechanism that has opening and closing transition times during which the light beam is partially illuminating by the photodiode, with the shutter mechanism being fully open for a period of time between the opening and closing transition times for fully illuminating the photodiode with the light beam, said method comprising steps of:
   integrating light illuminating by the photodiode by the light beam over a predetermined time interval beginning after the opening transition time when the shutter mechanism is fully open and ending prior to initiation of the closing transition time while the shutter mechanism is still fully open; and
   producing electrical signals corresponding to the light integrated by the photodiode over the predetermined time interval.

2. The method according to claim 1, wherein said integrating step includes electronically scanning the photodiode a first time at the beginning of the predetermined time interval to reset an electrical characteristic of the photodiode to an initial state, and integrating light on the photodiode over the predetermined time interval by allowing the electrical characteristic of the photodiode to change in dependence of the total amount of light incident on the photodiode over the predetermined time interval; and said producing step includes scanning the photodiode a second time at the end of the predetermined time interval to develop an electrical signal corresponding to a change in the electrical characteristic from the initial state.

3. The method according to claim 2, wherein said photodiode is sequentially illuminated by a plurality of light beams by way of the shutter mechanism and said photodiode is electronically scanned in accordance with said integrating and producing steps with respect to each light beam illuminating the photodiode, and said method further comprises scanning the photodiode a third time during a dark period occurring during a time between light beams illuminating the photodiode for resetting the electrical characteristic of the photodiode to minimize any carry-over effect due to a previous light beam illuminating the photodiode.

4. The method according to claim 2, wherein the electronic scanning is carried out according to a charge storage mode of operation, the electrical characteristic constitutes charge depletion of the p-n junction of the photodiode and said scanning steps include replenishing the charge depletion.

5. The method according to claim 2, wherein said photodiode is part of a photodiode array having a plurality of photodiodes and said first and second time scanning steps each include scanning all the photodiodes of the array in a serial fashion.

6. The method according to claim 2, wherein said photodiode constitutes a plurality of photodiodes arranged for being illuminated by spatially separate light beams by way of the shutter mechanism, with each photodiode being connected to a common electronic scanning circuit for being electronically scanned in accordance with said integrating and producing steps, wherein said method includes selectively setting the predetermined time interval for light integration for each photodiode so that electrical signals developed by said producing step from each of the photodiodes remains compatible with the common electronic scanning circuit.

7. A method for electronically scanning a photodiode array comprising a plurality of photodiodes in a charge storage mode of operation in which electrical charge is depleted from the p-n junction of a photodiode in dependence of the amount of light incident on the photodiode, the photodiode array being sequentially illuminated by individual light beams by way of a shutter mechanism that has opening and closing transition times during which a respective one of the beams is partially projected onto the array, with the shutter mechanism being fully open for a period of time between the opening and closing transition times for fully illuminating the photodiode with the respective light beam, said method comprising steps of:

scanning the photodiode array a first time after the opening transition period when the shutter mechanism is fully open for resetting the photodiodes of the array by replenishing depleted charge and starting a light integration period;

scanning the photodiode array a second time after a predetermined time interval and prior to initiation of the closing transition time to conclude the light integration period by replenishing depleted charge and measuring the amount of charge required to replenish the depleted charge for each photodiode at the conclusion of the light integration period;

storing a signal representing the measured amount of charge; and repeating the foregoing steps for each subsequent light beam projected onto the photodiode array by the shutter mechanism.

8. The method according to claim 7, and further comprising scanning the photodiode array a third time during a dark period between light beams projected onto the photodiode array by replenishing residual depleted charge.

9. The method according to claim 7, wherein there are a plurality of photodiode arrays connected to a common electronic scanning circuit for performing said method with respect to each said array, and said method further includes selectively setting the predetermined time interval for integrating light on each of the arrays.

10. A method for electronically scanning a time shared photodiode array that is sequentially illuminated by individual light beams by way of a shutter mechanism that has opening and closing transition times during which the individual light beams are partially projected onto the array, with the shutter mechanism being fully open for a period of time between the opening and closing transition times for fully illuminating the photodiode with the light beam, said method comprising steps of:

starting a light integration period for each light beam projected onto the photodiode array after the opening transition time when the shutter mechanism is fully open;

ending the light integration period after a predetermined time interval and before initiation of the closing transition time while the shutter mechanism is still fully open; and producing and storing signals corresponding to the light integrated by each of the photodiodes of the array at the end of the light integration period.

11. The method of claim 10, wherein said photodiode array comprises a plurality of photodiode arrays each being arranged for illumination by a different group of individual beams which are sequentially projected onto a respective one of the arrays, said integrating, producing and storing steps are performed with respect to each of said photodiode arrays, and said method further includes selectively setting the predetermined time interval for integrating the light beams on the respective photodiode arrays.

12. The method of claim 11, wherein the beams have intensities which vary from group to group and said setting step includes setting the predetermined time interval relatively longer for the photodiode arrays illuminated with beams of relatively lower intensity.

13. A method of electronically scanning a plurality of light integrating photodiode arrays, the arrays being repetitively illuminated by light beams in a predetermined sequence, comprising:

scanning the array a first time, in the predetermined sequence and while the respective arrays are being illuminated by the respective beams, to reset the photodiodes of each array to an initial state;

scanning each array a second time, after a predetermined interval from the first scanning and while the array is still illuminated by the respective beam, to produce a signal representing the amount of light integrated by the photodiodes of the array over the predetermined interval; and storing the signals produced by the second scanning step.

14. The method according to claim 13, and further including scanning each array a third time after the second scanning and during a dark period when the array is not illuminated by a light beam to reset the photodiodes of the array in the dark.

15. The method according to claim 13, and further including selectively setting the predetermined integration time interval for each array in dependence of the intensity of the respective light beams.

16. The method according to claim 10, wherein said starting light integration step includes electronically scanning the photodiode array a first time at the beginning of the predetermined time interval to reset an electrical characteristic of the respective photodiodes of the photodiode array to an initial state, and allowing light to be integrated on the photodiodes over the predetermined time interval by allowing the electrical characteristic of the respective photodiodes to change in dependence of the total amount of light incident on the photodiodes over the predetermined time interval; and said ending light integration step includes scanning the photodiode a second time at the end of the predetermined time interval to develop an electrical signal corresponding to a change in the electrical characteristic from the initial state.

17. The method according to claim 16, wherein said photodiode array is sequentially illuminated by a plurality of light beams by way of the shutter mechanism and said photodiode array is electronically scanned in accordance with said staring and ending light integrating and producing steps with respect to each light beam illuminating the photodiode array, and said method further comprises scanning the photodiode array a third time during a dark period occurring during a time between light beams illuminating the photodiode array for resetting the electrical characteristic of the photodiode to minimize any carry-over effect due to a previous light beam illuminating the photodiode array.

* * * * *